United States Patent [19]

Ariga et al.

[11] Patent Number: 5,624,639

[45] Date of Patent: Apr. 29, 1997

[54] GAS DETECTING DEVICE FOR VEHICLE

[75] Inventors: Katsuhiko Ariga, Oobu; Hiroaki Nishimura, Okazaki; Hideo Hattori, Chiryu, all of Japan

[73] Assignee: Nippondenso Co., Ltd., Kariya, Japan

[21] Appl. No.: 559,097

[22] Filed: Nov. 16, 1995

[30] Foreign Application Priority Data

Nov. 17, 1994 [JP] Japan .................................. 6-283166
Aug. 24, 1995 [JP] Japan .................................. 7-215632

[51] Int. Cl.⁶ .......................... G01N 27/00; G01N 27/12
[52] U.S. Cl. ........................ 422/83; 422/90; 422/114; 55/497
[58] Field of Search .................... 422/83, 62, 90, 422/93, 98, 114; 123/198 E; 55/280, 497, 511

[56] References Cited

U.S. PATENT DOCUMENTS

| 3,817,713 | 6/1974  | Ionescu .................... | 422/120 |
| 4,170,455 | 10/1979 | Henrie ...................... | 422/83  |
| 4,665,690 | 5/1987  | Nomoto et al. .......... | 60/286  |
| 4,772,454 | 9/1988  | Jarolics .................... | 422/83  |
| 5,059,221 | 10/1991 | McWilliam . |   |
| 5,314,828 | 5/1994  | Dalla Betta et al. ..... | 422/83  |
| 5,320,577 | 6/1994  | Tooru et al. ............. | 454/75  |

FOREIGN PATENT DOCUMENTS

| 9110325   | 12/1992 | Germany . |
| 4-123919  | 4/1992  | Japan . |
| 4-072009  | 6/1992  | Japan . |

*Primary Examiner*—Jeffrey Snay
*Attorney, Agent, or Firm*—Cushman, Darby & Cushman IP Group of Pillsbury Madison & Sutro, LLP

[57] ABSTRACT

A gas detecting device for a vehicle includes a casing which is formed therein with an air passage having an air inlet and an air outlet located above the air inlet. A filter is provided in the air passage below and downstream of a gas sensor. The filter has a lower end surface at a side of the air inlet and an upper end surface at a side of the gas sensor. The lower end surface of the filter works as an air-passing surface through which the air flows into the filter, while the upper end surface of the filter works as an air-passing surface through which the air flows out of the filter. A certain gap is provided between a lower portion of a side surface of the filter and an inner wall surface of the casing defining the air passage so that this lower portion of the filter also works as an air-passing surface through which the air flows into the filter. A labyrinth structure may be provided in the air passage between the air inlet and the filter for causing the air to meander at the labyrinth structure. Further, it may be arranged that the air passage has an opening area which is the greatest at the air inlet and then is gradually reduced as advancing toward the labyrinth structure.

7 Claims, 3 Drawing Sheets

GAS DETECTING DEVICE FOR VEHICLE

BACKGROUND OF THE INVENTION

1. Field of the Invention

The present invention relates to a gas detecting device installed in a vehicle for detecting a gas concentration in the air.

2. Description of the Prior Art

A gas detecting device for a vehicle has been proposed such as in Japanese First (unexamined) Utility Model Publication No. 4-72009 and Japanese First (unexamined) Patent Publication No. 4-123919, wherein a gas sensor is received in a casing which forms therein an air passage.

The gas detecting device of this type is provided with flow-velocity control sections at an inlet and an outlet of the casing for controlling an Air-flow velocity at substantially a constant small value. With this arrangement, even when a wind velocity outside the casing changes, a wind velocity within the casing (air passage) can be held substantially constant at a small value. Thus, the gas sensor arranged in the casing can detect a contamination degree of the air reliably without being affected by the wind velocity outside the casing.

On the other hand, in the foregoing gas detecting device, since the outside air flowing into the casing directly hits the gas sensor, it is highly possible that dust in the air adheres to a detecting surface of the gas sensor and that the detecting surface is subjected to invasion of water or moisture.

In view of this, it has been proposed to arrange a filter upstream of the gas sensor. The filter has an air-inlet side end surface, an air-outlet side end surface and side surfaces extending along the air passage and connecting the air-inlet side end surface and the air-outlet side end surface to each other. The air is introduced into the air passage via the inlet of the casing and flows into the filter via the air-inlet side end surface and out of the filter via the air-outlet side end surface. When the moisture or water enters the air passage via the inlet of the casing to wet the filter, a water film is likely to be formed at the air-inlet side end surface of the filter so that the air-inlet side end surface of the filter can not be used as an air-passing surface. As a result, the necessary air is not supplied to the gas sensor so that accurate detection of a gas concentration is rendered difficult.

SUMMARY OF THE INVENTION

Therefore, it is an object of the present invention to provide an improved gas detecting device for a vehicle which allows air to pass through a filter and thus achieves accurate detection of a gas concentration in the air even when the filter is subjected to invasion of moisture or water.

According to one aspect of the present invention, a gas detecting device for a vehicle comprises a casing having therein an air passage, the air passage having an air Inlet where air flows in and an air outlet where the air flows out; a filter arranged in the air passage between the air inlet and the air outlet, the filter having a first end surface at a side of the air inlet, a second end surface at a side of the air outlet, and a side surface extending along the air passage and connecting the first and second end surfaces; and a gas sensor for detecting a gas concentration in the air introduced into the air passage through the air inlet and having passed through the filter, wherein a given gap is provided at least between a portion of the side surface located at a side of the first end surface and an inner wall surface of the casing defining the air passage, and wherein the air flows into the filter through the first end surface and the portion of the side surface and flows out of the filter through the second end surface.

BRIEF DESCRIPTION OF THE DRAWINGS

The present invention will be understood more fully from the detailed description given hereinbelow, taken in conjunction with the accompanying drawings.

In the drawings.

DESCRIPTION OF THE PREFERRED EMBODIMENT

Now, a preferred embodiment of the present invention will be described hereinbelow with reference to the accompanying drawings.

Figure 1:
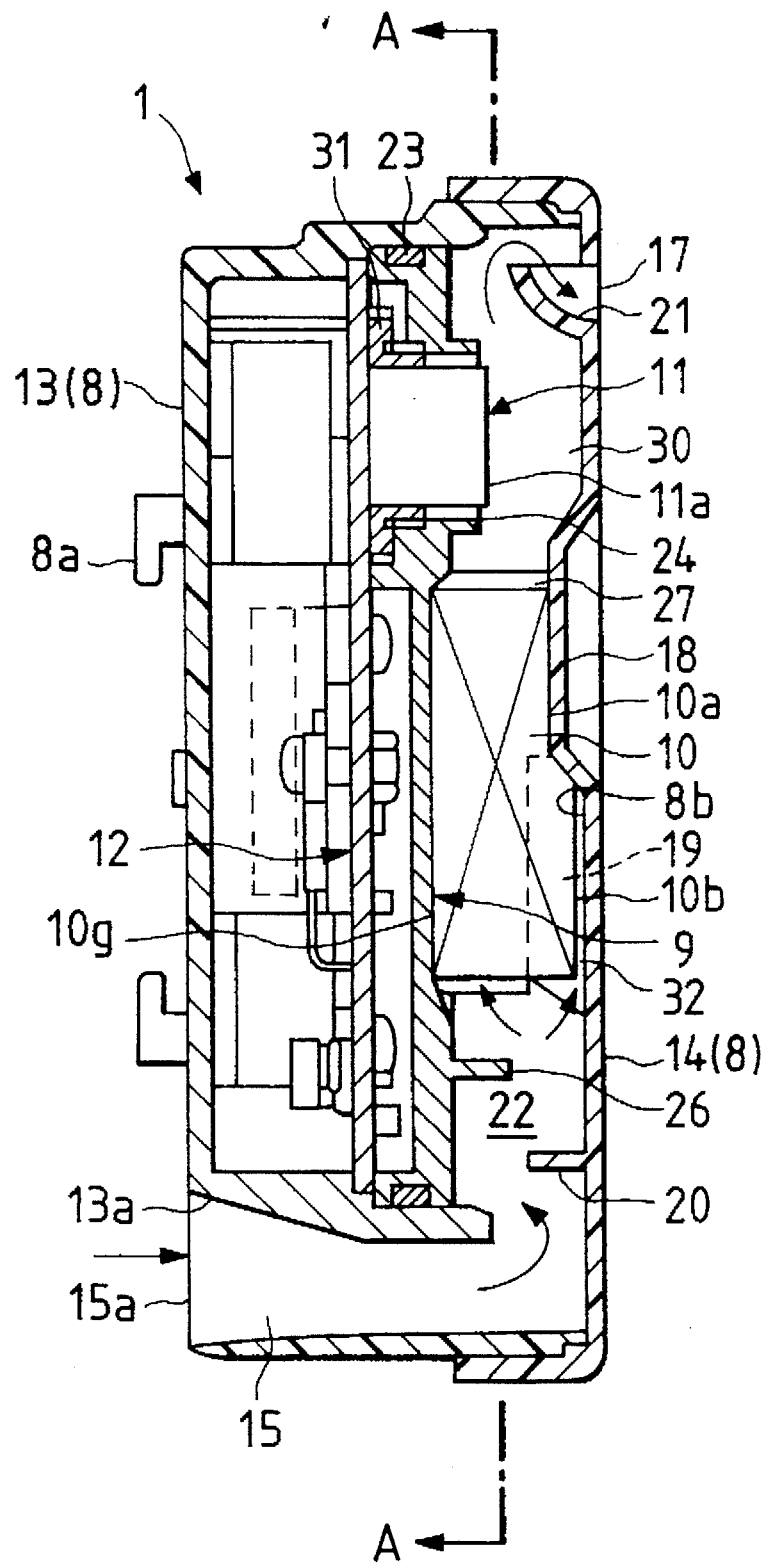
FIG. 1 is a side sectional view of a gas detecting device for a vehicle according to a preferred embodiment of the present invention.
Figure 2:
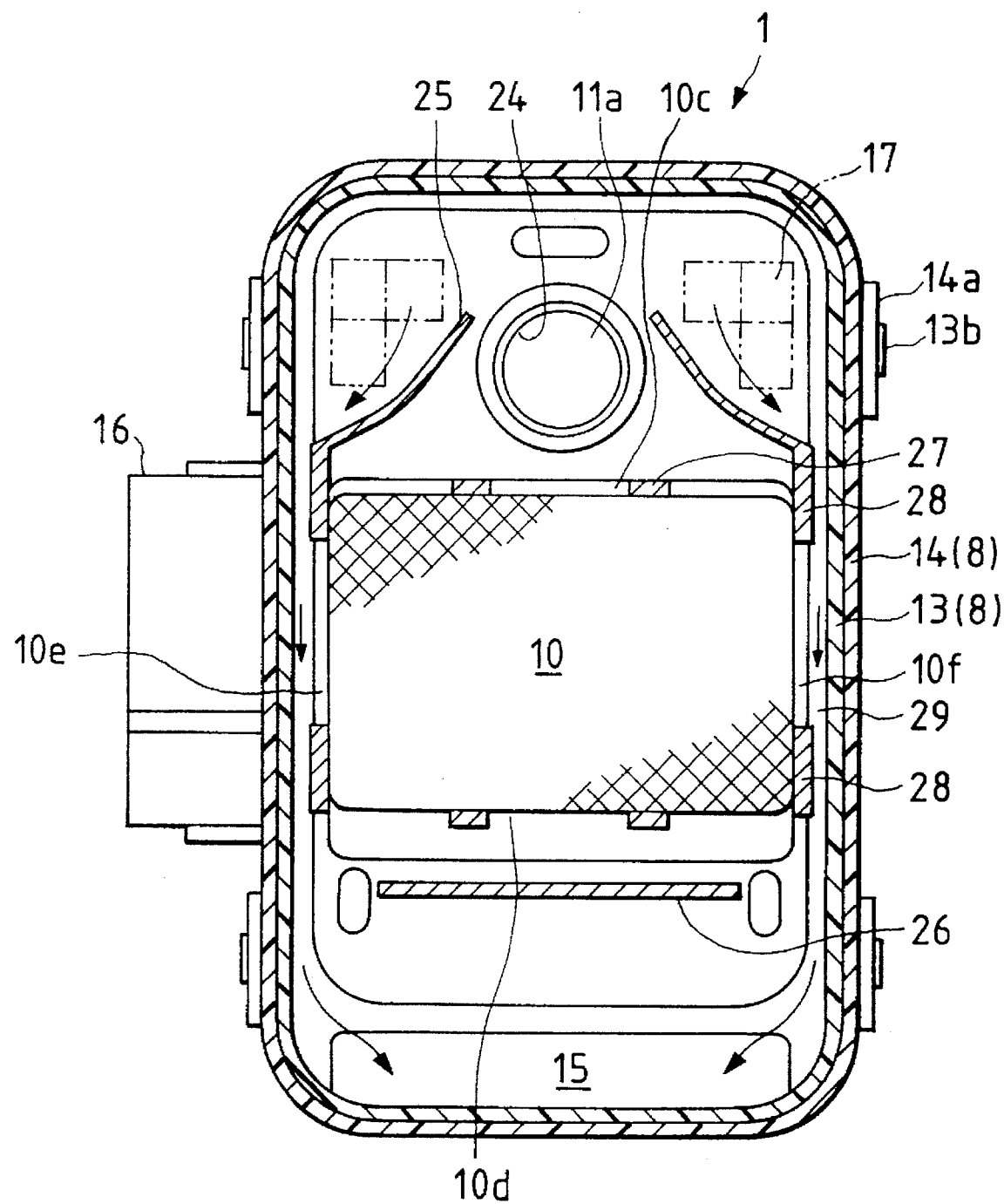
FIG. 2 is a sectional view taken along line A—A in FIG. 1.

FIG. 1 is a side sectional view of a gas detecting device 1 for a vehicle according to the preferred embodiment of the present invention, and FIG. 2 is a sectional view taken along line A—A in FIG. 1.

Figure 3:
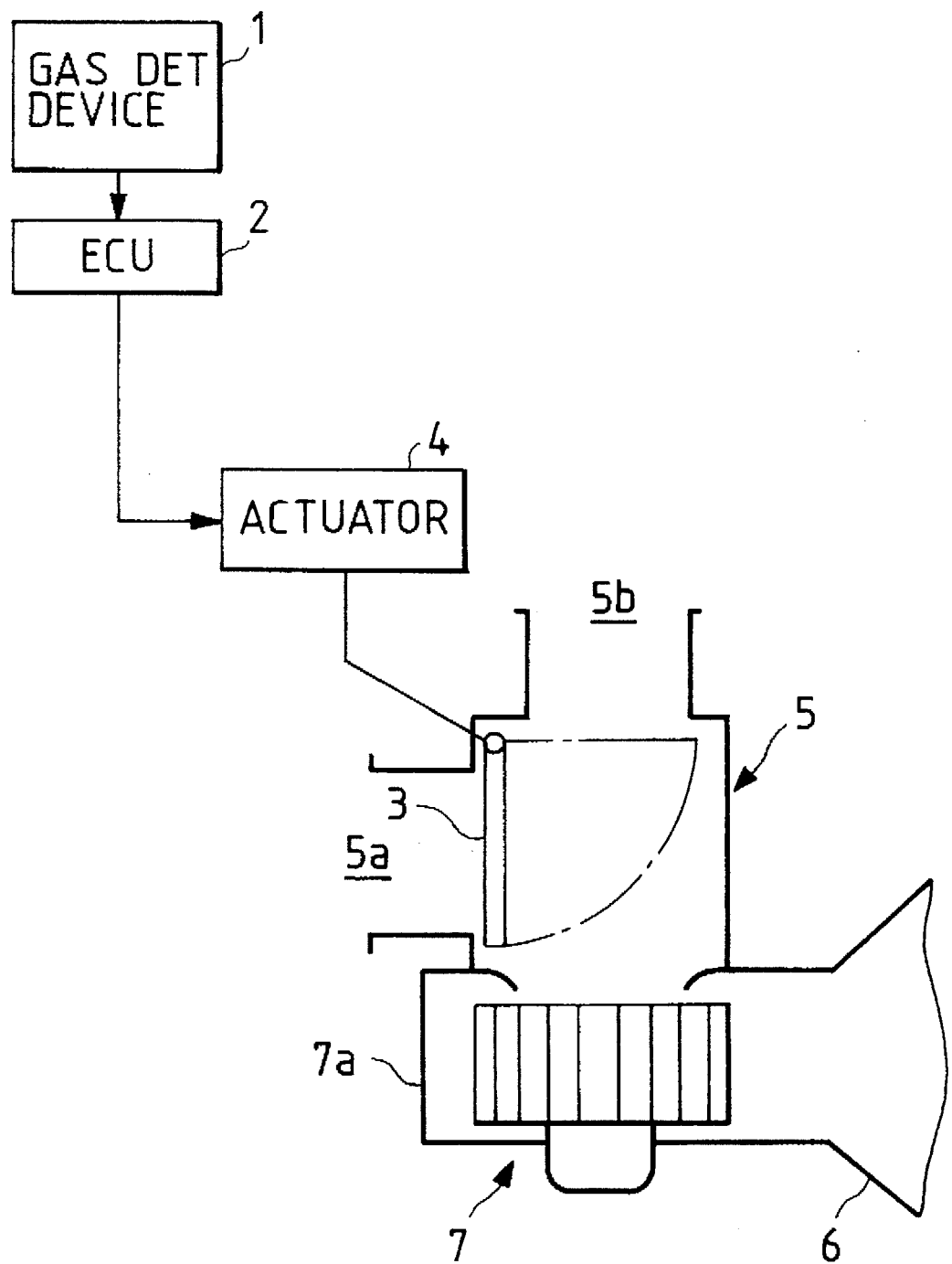
FIG. 3 is a diagram schematically showing an inside/outside air switching device which is operated depending on a gas concentration monitored by the gas detecting device shown in FIGS. 1 and 2.

The gas detecting device 1 detects a gas concentration (a concentration of stinking gas components, such as HC and NOx) in the outside air, and outputs a detection signal indicative of the detected gas concentration to an ECU (electronic control unit) 2 installed in the vehicle as shown in FIG. 3. As further shown in FIG. 3, the ECU 2, in response to the detection signal from the gas detecting device 1, outputs a control signal to an actuator 4 for actuating an inside/outside air switching damper 3 of an inside/outside air switching device.

As shown in FIG. 3, the inside/outside air switching device includes the inside/outside air switching damper 3 which selectively opens/closes an inside-air introducing port 5a and an outside-air introducing port 5b formed in an inside/outside air switching box 5. The inside/outside air switching device further includes the actuator 4, in the form of such as a servomotor, which actuates the inside/outside air switching damper 3. The inside/outside air switching box 5 is arranged at an upstream end of a duct 6 which conducts the air toward a vehicle compartment, and is formed integral with a blower case 7a of an air blower 7.

The gas detecting device 1 is disposed, for example, between a radiator grille (not shown) and a radiator (not shown) of the vehicle and attached to the radiator grille via mounting hooks 8a (see FIG. 1) provided at a front side of a casing 8 of the gas detecting device 1.

Hereinafter, upper and lower directions in FIGS. 1 and 2 represent skyward and groundward directions, respectively, of the gas detecting device 1 when mounted on the radiator grille.

The gas detecting device 1 includes the foregoing casing 8, a separator 9, a filter 10, a gas sensor 11, a circuit board 12 and others.

The casing 8 is composed of a resinous housing 13 and a resinous cover 14. The housing 13 has a box shape and is formed at its lower end with an air introducing passage 15 for introducing the outside air in a backward (rightward in FIG. 1) direction from a front side of the housing 13.

The air introducing passage 15 has an opening area (cross-sectional area) which is the greatest at an air inlet 15a opened at the front side of the housing 13 and which is then gradually reduced as advancing inward (backward) from the air inlet 15a. Specifically, a passage wall 13a of the housing 13 defining an upper side of the air introducing passage 15 is inclined downward from the air inlet 15a.

A connector 16 (see FIG. 2) is fixed to a side surface of the housing 13 for connection to the ECU 2.

The cover 14 is fitted over the outer periphery of the housing 13 and fixed to the housing 13 by engagement between claws 13b provided on the outer periphery of the housing 13 and hooks 14a provided on the outer periphery of the cover 14.

The cover 14 is provided with air outlets 17, a filter pressing portion 18, a presser rib 19 and a water-drip wall 20.

The air outlets 17 are provided at three locations at each of both upper sides, in a width direction, of the cover 14 as shown in FIG. 2. A water-guard wall 21 is provided at each of the air outlets 17 for preventing invasion of moisture or water into the casing 8 through the corresponding air outlet 17. The water-guard wall 21 is formed by a portion of the cover 14 which extends inward of the casing 8 in a bent fashion.

The filter pressing portion 18 is formed by a portion of the cover 14 which is recessed inward at a position below the air outlets 17. The filter pressing portion 18 presses and holds an upper side surface 10a of the filter 10 accommodated in the casing 8.

The presser rib 19 is in the form of an inward projection of the cover 14 and extends vertically below the filter pressing portion 18. The presser rib 19 partly presses and holds a lower side surface 10b of the filter 10.

The water-drip wall 20 is in the form of an inward projection of the cover 14 and extends in the width direction of the cover 14 below the presser rib 19. The water-drip wall 20 is provided for achieving a labyrinth structure of a later-described air passage 22.

The separator 9 is fixed inside the housing 13 via an O-ring 23 interposed between the outer periphery of the separator 9 and the inner periphery of the housing 13. The separator 9 divides the inside of the casing 8 into a board side where the circuit board 12 is arranged and a passage side where the introduced outside air flows. At the passage side, the air passage 22 is formed between the separator 9 and the cover 14 for communication between the air inlet 15a and the air outlets 17. The foregoing air introducing passage 15 forms a portion of the air passage 22.

The separator 9 is provided with a communication hole 24, drain walls 25 (see FIG. 2), filter supporting sections and a water-drip wall 26.

The communication hole 24 is formed at an upper center portion of the separator 9 for receiving therethrough the gas sensor 11 so that the gas sensor 11 penetrates from the board side to the passage side.

The drain walls 25 are provided at right and left sides, in FIG. 2, of the communication hole 24 so as to approach each other as advancing upward. Lower ends of the drain walls 25 extend downward along inner lateral walls of the housing 13.

The filter supporting sections include four projections 27 which engage an upper end surface 10c and a lower end surface 10d of the filter 10 for positioning the filter 10 in a vertical direction. The filter supporting sections further include four lateral walls 28 which engage lateral walls 10e and 10f of the filter 10 for positioning the filter 10 in a lateral or width direction. As seen from FIG. 2, among the four lateral walls 28, the upper two lateral walls 28 are formed by the portions of the drain walls 25 which extend downward along the inner lateral walls of the housing 13, respectively. As further seen from FIG. 2, drain passages 29 are formed at both lateral sides of the filter 10 between the lateral walls 28 and the corresponding inner lateral walls of the housing 13.

The water-drip wall 26 is in the form of a projection of the separator 9 and extends in the width direction at a vertical position between the presser rib 19 and the water-drip wall 20 of the cover 14. The water-drip wall 26, in cooperation with the water-drip wall 20, renders the air passage 22 labyrinthine.

The filter 10 is provided for removing dust contained in the introduced outside air. The filter 10 is a resilient solid body formed by binding a fibrous material in a known manner and having proper space inside thereof. The filter 10 is held in an upright posture at the passage side of the separator 9 by means of the foregoing projections 27 and lateral walls 28, and fixed under pressure between the separator 9 and the cover 14 by means of the filter pressing portion 18 and the presser rib 19. Specifically, the upper side surface 10a of the filter 10 is pressed in its entirety by the filter pressing portion 18, while the lower side surface 10b of the filter 10 is partially pressed by the presser rib 19.

As shown in FIG. 1, a certain gap 32 is provided between the lower side surface 10b of the filter 10 and an inner wall surface 8b of the cover 14 due to the presser rib 19 pressing inward the lower side surface 10b of the filter 10. Accordingly, the lower end surface 10d and the lower side surface 10b facing the gap 32 are arranged to work as inlet-side air-passing surfaces of the filter 10 where the air flows in, while the upper end surface 10c is arranged to work as an outlet-side air-passing surface where the air flows out. As appreciated from FIG. 1, a vertical length of the filter 10 (a sum of vertical lengths of the upper and lower side surfaces 10a and 10b) is greater than a sum of lengths of the upper and lower end surfaces 10c and 10d in a fight/left direction in FIG. 1.

The gas sensor 11 includes a detector element (not shown) in the form of a metal oxide semiconductor (for example, formed of SnO2 as a main component added with a small quantity of noble metal), and a heater (not shown) for heating the detector element to high temperatures. The detector element has a characteristic to change its electrical resistance when the particular gas components get in touch with a detecting surface 11a thereof while being held at the high temperatures, and outputs a gas concentration in the air in the form of an electric signal (voltage signal). Accordingly, an output voltage variation of the gas sensor 11 is increased as a gas concentration in the air is increased.

The gas sensor 11 is attached to the circuit board 12 and extends out to the passage side through the communication hole 24 of the separator 9 so that the detecting surface 11a of the detector element is exposed to the air passage 22. An air-stay space 30 is formed around the detecting surface 11a so as to allow the air flowing in the air passage 22 to easily stay thereat temporarily.

The communication hole 24 is hermetically sealed relative to the gas sensor 11 by a grommet 31 mounted on the outer periphery of the gas sensor 11.

The circuit board 12 includes a signal processing circuit (not shown) for digitizing an analog voltage detection signal from the gas sensor 11 and outputs a digital detection signal digitized via the signal processing circuit to the ECU 2. The circuit board 12 is fixedly disposed in an upright posture at the board side of the separator 9 and connected to built-in terminals (not shown) of the connector 16.

Now, an operation of this embodiment will be described hereinbelow.

The outside air introduced into the air introducing passage 15 via the air inlet 15a meanders through the labyrinth structure of the air passage 22. The air then passes through the filter 10 where dust contained in the air is removed. Subsequently, the air temporarily stays at the air-stay space 30 and then flows out to the exterior of the casing 8 via the air outlets 17. The gas sensor 11 detects a gas concentration in the air staying at the air-stay space 30 and outputs a detection signal indicative of the detected gas concentration to the ECU 2 via the foregoing signal processing circuit of the circuit board 12.

In this embodiment, as described before, the given gap 32 is provided between the lower side surface 10b of the filter 10 and the inner wall surface 8b of the cover 14 so that the air having passed through the labyrinth structure of the air passage 22 flows into the filter 10 through both the lower end surface 10d and the lower side surface 10b and then flows out through the upper end surface 10c. Thus, even when moisture or water enters the air passage 22 via the air inlet 15a to moisten or wet the filter 10 so that a water film is formed at the lower end surface 10d to disable the air from entering the filter 10 via the lower end surface 10d, the air still can be introduced into the filter 10 via the lower side surface 10b. Accordingly, the air permeability of the filter 10 is ensured to achieve the accurate detection of the gas concentration in the air.

Further, as described before, the air introducing passage 15 has the opening area which is the greatest at the air inlet 15a and then is gradually reduced as advancing inward from the air inlet 15a. Accordingly, a wind velocity of the air introduced via the air inlet 15a is efficiently converted to a pressure within the air introducing passage 15. Thus, even if the water-drip walls 20 and 26 forming the labyrinth structure are provided downstream of the filter 10, an air-flow loss can be suppressed due to this conversion to the pressure so that the air can be fed to the gas sensor 11 through the filter 10 in an amount sufficient for detecting the gas concentration.

Further, since the labyrinth structure is provided in the air passage 22 below the filter 10, even when moisture or water is contained in the air introduced via the air introducing passage 15, invasion of the moisture or water can be prevented by the water-drip walls 20 and 26 forming the labyrinth structure. Specifically, when the air containing the moisture or water goes upward to pass through the labyrinth structure, the moisture or water hits the water-drip walls 20 and 26 and falls downward so as to be discharged via the air inlet 15a of the air introducing passage 15.

On the other hand, the moisture or water reaching the filter 10 can be prevented from diffusing over the entirety of the filter 10 by properly selecting a thickness of the fiber forming the filter 10 and a clogging mount of the filter 10 per unit volume. In this embodiment, the upper side of the filter 10 is pressed by the filter pressing portion 18 so as to be contracted as a whole in a thickness direction (leftward in FIG. 1), while the lower side of the filter 10 is pressed by the presser rib 19 so as to be partly contracted in the thickness direction so that the other portions thereof are not so contracted. Thus, meshes of the lower side of the filter 10 are larger (rougher) as compared with those of the upper side of the filter 10. This mesh arrangement as well as the foregoing clogging mount selection per unit volume of the filter 10 prevent the moisture or water from diffusing over the entirety of the filter 10. Specifically, since meshes of the filter 10 are larger (rougher) at the lower side thereof as compared with the upper side thereof, the moisture or water in the filter 10 is not liable to go upward and pass through the upper side of the filter 10 for reaching the gas sensor 11, but liable to stay at the lower end portion of the filter 10 due to its own clogging mount.

When a quantity of the moisture or water staying at the lower end portion of the filter 10 is increased, the moisture or water drips down and flows out via the air inlet 15a. Accordingly, although the lower end surface 10d of the filter 10 can not be used as an air-passing surface due to formation of the water film, the lower side surface 10b of the filter 10 can be used as an air-passing surface. Thus, the permeability of the filter 10 is ensured even when the filter 10 is subjected to invasion of the moisture or water so that the normal detection of the gas concentration can be performed using the gas sensor 11.

Further, if the entirety of the gas detecting device 1 is subjected to the moisture or water to allow invasion of the moisture or water into the casing 8 via a gap at the engaging portion between the housing 13 and the cover 14, the invaded moisture or water can be discharged through the drain passages 29 formed at both lateral sides of the filter 10.

On the other hand, when the air outlets 17 are subjected to the moisture or water, invasion of the moisture or water into the casing 8 can be prevented by the water-guard walls 21. Further, even if the moisture or water enters the casing 8 via the air outlets 17 and the water-guard walls 21, the invaded moisture or water is received by the drain walls 25 and guided to the drain passages 29 so that the gas sensor 11 is prevented from being subjected to the moisture or water.

In the foregoing preferred embodiment, the certain gap 32 is formed between the lower side surface 10b of the filter 10 and the cover 14 for using the lower side surface 10b as an air-passing surface. On the other hand, a certain gap may be formed between the separator 9 and a side surface 10g (only at a lower side thereof) of the filter 10 facing the separator 9 so as to use the lower side of the side surface 10g as an air-passing surface, instead of or in addition to the lower side surface 10b.

Further, in the foregoing preferred embodiment, the inside/outside air switching device is controlled depending on a gas concentration of the outside air monitored by the gas detecting device 1. On the other hand, it may also be arranged that the gas detecting device 1 is Installed in the vehicle compartment to monitor a gas concentration in the inside air (air in the vehicle compartment) and that an air cleaner is controlled to be operated when a degree of contamination of the inside air is high. Alternatively, it may also be arranged that the inside/outside air switching device Is controlled to set an outside air mode when a degree of contamination of the inside air is high.

While the present invention has been described in terms of the preferred embodiment, the invention is not to be limited thereto, but can be embodied in various ways without departing from the principle of the invention as defined in the appended claims.

What is claimed is:

1. A gas detecting device for a vehicle comprising:

a casing having therein an air passage, said air passage having an air inlet where air flows in and an air outlet where the air flows out;

a filter arranged in said air passage between said air inlet and said air outlet, said filter having a first end surface at a side of said air inlet, a second end surface at a side of said air outlet, and a side surface extending along said air passage and connecting said first and second end surfaces; and a gas sensor for detecting a gas concentration in the air introduced into said air passage through said air inlet and having passed through said filter;

wherein a given gap is provided at least between a portion of said side surface located at a side of said first end surface and an inner wall surface of said casing defining said air passage, and wherein the air flows into said filter through said first end surface and said portion of the side surface and flows out of said filter through said second end surface.

2. The gas detecting device according to claim 1, wherein said first end surface of the filter is arranged at a position below said second end surface of the filter.

3. The gas detecting device according to claim 1, wherein meshes of said filter are larger at the side of said first end surface than at a side of said second end surface.

4. The gas detecting device according to claim 1, wherein a labyrinth structure is provided in said air passage between said air inlet and said filter for suppressing invasion of moisture or water through said air inlet.

5. The gas detecting device according to claim 4, wherein said air passage has an air introducing section extending between said air inlet and said labyrinth structure, said air introducing section having an opening area which is the greatest at said air inlet and is gradually reduced as advancing toward said labyrinth structure.

6. The gas detecting device according to claim 1, wherein said casing is provided therein with a drain passage and a drain wall for guiding moisture or water entering said casing through said air outlet to said drain passage.

7. The gas detecting device according to claim 6, wherein a detecting surface of said gas sensor is exposed within said air passage between said filter and said air outlet, and wherein said drain wall is provided between said air outlet and said detecting surface of the gas sensor and extends to said drain passage.

* * * * *